United States Patent
Paolini et al.

(10) Patent No.: US 7,794,419 B2
(45) Date of Patent: Sep. 14, 2010

(54) APPARATUS FOR CONTROLLING BLOOD FLOW IN AN EXTRACORPOREAL CIRCUIT

(75) Inventors: Francesco Paolini, Ganaceto (IT); Carlo Alberto Lodi, Carpi (IT); Francesco Fontanazzi, Modena (IT)

(73) Assignee: Gambro Lundia AB, Lund (SE)

( * ) Notice: Subject to any disclaimer, the term of this patent is extended or adjusted under 35 U.S.C. 154(b) by 463 days.

(21) Appl. No.: 11/913,786

(22) PCT Filed: May 18, 2005

(86) PCT No.: PCT/IB2005/001347
§ 371 (c)(1),
(2), (4) Date: Nov. 7, 2007

(87) PCT Pub. No.: WO2006/123197
PCT Pub. Date: Nov. 23, 2006

(65) Prior Publication Data
US 2008/0275377 A1    Nov. 6, 2008

(51) Int. Cl.
*A61M 37/00*   (2006.01)
*C02F 1/44*    (2006.01)

(52) U.S. Cl. .............. 604/6.06; 604/6.09; 604/6.11; 210/645; 210/741

(58) Field of Classification Search ............... 604/4.01, 604/5.01, 5.04, 6.09, 6.11, 6.06; 210/645, 210/646, 739, 741
See application file for complete search history.

(56) References Cited

U.S. PATENT DOCUMENTS

| 2,709,785 A | 5/1955 | Fielden |
| 3,324,720 A | 6/1967 | Sutherland |
| 3,396,331 A | 8/1968 | Sperry, III |
| 3,404,336 A | 10/1968 | Rosenthal |
| 3,433,935 A | 3/1969 | Sherman |
| 3,446,073 A | 5/1969 | Auphan et al. |

(Continued)

FOREIGN PATENT DOCUMENTS

DE    4024434    2/1992

(Continued)

OTHER PUBLICATIONS

Robert L. Hester, Ph.D., "A new Technique for Determining Recirculation in the ESRD Patient", Nephrology News & Issues, pp. 44-55, Jun. 1993, Jackson, MS.

(Continued)

*Primary Examiner*—Leslie R Deak
(74) *Attorney, Agent, or Firm*—Pearne & Gordon LLP (57) ABSTRACT

The apparatus for blood flow control in an extracorporeal circuit comprises: a user interface for setting a desired blood flow value ($q_{bREAL}$) and a datum relating to the vascular access, a memory for recording a plurality of mathematical relations having mathematical expressions relating to the vascular access organ to be used, and a control unit. The control unit identifies the vascular access, selects, from among the plurality of mathematical relations present in the memory, a relation which corresponds to the vascular access identified, and calculates, as a mathematical function of the set value for the desired flow ($q_{bREAL}$), a value at which to set the angular velocity of the pump associated to the extracorporeal circuit and/or a theoretical value of the arterial pressure upstream of the pump.

15 Claims, 2 Drawing Sheets

U.S. PATENT DOCUMENTS

| | | |
|---|---|---|
| 3,450,984 A | 6/1969 | Holmes |
| 3,482,575 A | 12/1969 | Claff et al. |
| 3,491,592 A | 1/1970 | Evers et al. |
| 3,545,428 A | 12/1970 | Webster, Jr. |
| 3,561,266 A | 2/1971 | Auphan et al. |
| 3,604,263 A | 9/1971 | Auphan et al. |
| 3,619,423 A | 11/1971 | Snider et al. |
| 3,640,271 A | 2/1972 | Horton |
| 3,722,276 A | 3/1973 | Chandler et al. |
| 3,733,899 A | 5/1973 | Auphan et al. |
| 3,867,688 A | 2/1975 | Koski et al. |
| 3,882,861 A | 5/1975 | Kettering et al. |
| 3,964,479 A | 6/1976 | Boag et al. |
| 3,980,946 A | 9/1976 | Fleury |
| 3,985,134 A | 10/1976 | Lissot et al. |
| 3,987,788 A | 10/1976 | Emil |
| 4,081,372 A | 3/1978 | Atkin et al. |
| 4,136,563 A | 1/1979 | Mueller et al. |
| 4,138,639 A | 2/1979 | Hutchins |
| 4,153,418 A | 5/1979 | Haas |
| 4,167,870 A | 9/1979 | Haas |
| 4,181,610 A | 1/1980 | Shintani et al. |
| 4,361,049 A | 11/1982 | Volgyesi |
| 4,391,124 A | 7/1983 | Drost et al. |
| 4,432,231 A | 2/1984 | Napp et al. |
| 4,434,648 A | 3/1984 | Drost et al. |
| 4,446,871 A | 5/1984 | Imura |
| 4,508,622 A | 4/1985 | Polaschegg et al. |
| 4,650,458 A | 3/1987 | Dahlberg et al. |
| 4,715,849 A | 12/1987 | Gion et al. |
| 4,739,492 A | 4/1988 | Cochran |
| 4,740,755 A | 4/1988 | Ogawa |
| 4,777,938 A | 10/1988 | Sirota |
| 4,797,655 A | 1/1989 | Orndal et al. |
| 4,822,341 A | 4/1989 | Colone |
| 4,825,168 A | 4/1989 | Ogawa et al. |
| 4,856,321 A | 8/1989 | Smalling et al. |
| 4,885,001 A | 12/1989 | Leppert |
| 4,885,087 A | 12/1989 | Kopf |
| 4,923,598 A | 5/1990 | Schal |
| 4,995,268 A | 2/1991 | Ash et al. |
| 5,004,459 A | 4/1991 | Peabody et al. |
| 5,024,756 A | 6/1991 | Sternby |
| 5,057,278 A | 10/1991 | Maxwell et al. |
| 5,058,416 A | 10/1991 | Engelhardt et al. |
| 5,092,836 A | 3/1992 | Polaschegg |
| 5,098,373 A | 3/1992 | Polaschegg |
| 5,100,554 A | 3/1992 | Polaschegg |
| 5,230,341 A | 7/1993 | Polaschegg |
| 5,312,550 A | 5/1994 | Hester |
| 5,357,967 A | 10/1994 | Dixon et al. |
| 5,372,136 A | 12/1994 | Steuer et al. |
| 5,372,709 A | 12/1994 | Hood |
| 5,442,969 A | 8/1995 | Troutner et al. |
| 5,453,576 A | 9/1995 | Krivitski |
| 5,507,723 A | 4/1996 | Keshaviah |
| 5,510,716 A | 4/1996 | Buffaloe et al. |
| 5,510,717 A | 4/1996 | Buffaloe et al. |
| 5,518,623 A | 5/1996 | Keshaviah et al. |
| 5,570,026 A | 10/1996 | Buffaloe et al. |
| 5,588,959 A | 12/1996 | Ahmad et al. |
| 5,595,182 A | 1/1997 | Krivitski |
| 5,605,630 A | 2/1997 | Shibata |
| 5,644,240 A | 7/1997 | Brugger |
| 5,662,806 A | 9/1997 | Keshaviah et al. |
| 5,685,988 A | 11/1997 | Malchesky |
| 5,685,989 A | 11/1997 | Krivitski et al. |
| 5,733,257 A | 3/1998 | Sternby |
| 5,830,365 A | 11/1998 | Schneditz |
| 5,866,015 A | 2/1999 | Kramer |
| 5,894,011 A | 4/1999 | Prosl et al. |
| 5,900,726 A | 5/1999 | Brugger et al. |
| 5,902,253 A | 5/1999 | Pfeiffer et al. |
| 5,947,692 A | 9/1999 | Sahlin et al. |
| 6,061,590 A | 5/2000 | Krivitski |
| 6,090,048 A | 7/2000 | Hertz et al. |
| 6,117,099 A | 9/2000 | Steuer et al. |
| 6,153,109 A | 11/2000 | Krivitski |
| 6,177,049 B1 | 1/2001 | Schnell et al. |
| 6,189,388 B1 | 2/2001 | Cole et al. |
| 6,210,591 B1 | 4/2001 | Krivitski |
| 6,221,040 B1 | 4/2001 | Kleinekofort |
| 6,308,737 B1 | 10/2001 | Krivitski |
| 6,623,443 B1 | 9/2003 | Polaschegg |
| 6,827,698 B1* | 12/2004 | Kleinekofort ............. 604/6.06 |
| 7,172,570 B2* | 2/2007 | Cavalcanti et al. ......... 604/6.11 |
| 2001/0031222 A1 | 10/2001 | Schnell et al. |
| 2001/0050256 A1 | 12/2001 | Krivitski |
| 2010/0145302 A1* | 6/2010 | Cull et al. .................. 604/505 |

FOREIGN PATENT DOCUMENTS

| | | |
|---|---|---|
| DE | 19537688 | 5/1996 |
| DE | 19528907 | 11/1996 |
| DE | 19541783 | 3/1997 |
| DE | 19901078 | 2/2000 |
| EP | 0018817 A1 | 11/1980 |
| EP | 0097366 | 1/1984 |
| EP | 0104896 A2 | 4/1984 |
| EP | 0272414 | 6/1988 |
| EP | 0315312 A1 | 5/1989 |
| EP | 0547025 A1 | 6/1993 |
| EP | 0089003 A2 | 9/1993 |
| EP | 0590810 A1 | 4/1994 |
| EP | 0658352 | 6/1995 |
| EP | 0693296 A1 | 1/1996 |
| EP | 0693297 A1 | 1/1996 |
| EP | 0723463 | 7/1996 |
| EP | 0773035 | 5/1997 |
| EP | 0835669 A2 | 4/1998 |
| EP | 0845273 | 6/1998 |
| EP | 0900094 | 3/1999 |
| EP | 0920877 A1 | 6/1999 |
| EP | 0928614 A1 | 7/1999 |
| EP | 0943369 | 9/1999 |
| EP | 1020199 | 7/2000 |
| EP | 1044695 | 10/2000 |
| EP | 1106191 A1 | 6/2001 |
| ES | 2026508 | 5/1992 |
| FR | 2244546 | 4/1975 |
| GB | 2093192 A | 8/1982 |
| JP | 60190873 | 9/1985 |
| JP | 5236990 | 9/1993 |
| SU | 521891 | 10/1976 |
| SU | 1013853 A | 5/1981 |
| WO | 90/06781 | 6/1990 |
| WO | 91/09229 | 6/1991 |
| WO | 9608305 A1 | 3/1996 |
| WO | 97/01289 | 1/1997 |
| WO | 97/10013 | 3/1997 |
| WO | 98/17193 | 4/1998 |
| WO | 98/17334 | 4/1998 |
| WO | 98/32477 | 7/1998 |
| WO | 99/64088 | 12/1999 |
| WO | 00/18451 | 4/2000 |
| WO | 00/74732 A1 | 12/2000 |
| WO | 01/08719 A2 | 2/2001 |
| WO | 02/04044 A1 | 1/2002 |
| WO | 03/055542 A1 | 7/2003 |
| WO | 2004/067064 A1 | 8/2004 |

WO 2005/042066 A1 5/2005

OTHER PUBLICATIONS

Petitclerc et al., "A model for non-invasive estimation of in vivo dialyzer performances and patient's conductivity during hemodialysis", The International Journal of Artificial Organs—vol. 16—No. 8, 1993—pp. 585-591.

Petitclerc et al. "Non-invasive monitoring of effective dialysis dose delivered to the hemodialysis patient"—Nephrology Dialysis Transplantation (1995) 10: pp. 212-216.

Mercadal et al. "Determination of access blood flow from ionic dialysance: Theory and validation"—Kindney International, vol. 56 (1999), pp. 1560-1565.

Gambro, "FAM 10 Fistula Flow Studies and Their Interpretation", pp. 1-31, Lund Sweden, published on or before Sep. 29, 1991.

Salomon et al. Translation: "Low frequency electrodeless conductometer for measuring the electrical conductivity of solutions", 1959, p. 1-13, Industrial Group Headquarters, Risley, Warrington, Lancashire, GB.

Richard A. Sherman, "Recirculation Revisited", Seminars in Dialysis, vol. 4, No. 4, pp. 221-223, Oct.-Dec. 1991, New Jersey.

McKamy Smith, "Cardiac Output Determined by the Saline Conductivity Method Using an Extraarterial Conductivity Cell", Cardiovascular Research Center Bulletin, vol. 5, No. 4, pp. 123-134, Apr.-Jun. 1967, Texas.

Mogens Thomsen et al., "Evaluation of Clinical Examination Preceding Surgical Treatment of AV Fistula problems", Acta Chir Scand, vol. 151, pp. 133-137, 1985, Sweden.

Transonic Systems, Inc., "Access Flow & Recirculation Measured During Hemodialysis", Oct. 1994, 7 pages, N.Y.

C. Aldridge et al., "The Assessment of Arteriovenous Fistulae Created for Hemodialysis from Pressure and Thermal Dilution Measurements", Journal of Medical Engeneering & Technology, vol. 8, No. 3, pp. 118-124, May/Jun. 1984, U. K.

C. Aldridge, et al., "Instrument Design for the Bedside Assessment of Arteriovenous Fistulae in Hemodialysis Patients", Proceedings EDTNE-ERCA, vol. 14, pp. 255-260, 1985, UK.

Joseph J. Carr, "Integration of Decaying Exponential Sensor Output Signals", Sensors, pp. 28-34, Jul. 1989, Virginia.

J. Daugirdas, "The Fourth Annual Advanced Dialysis Technical Symposium", Dialysis & Transplantation, vol. 17, No. 8, pp. 432-433, Aug. 1998, Illinois.

Fresenius "BTM 4008", Nov. 1993, 7 pages, Germany and translation from German to English.

Gambro, "Fistula Assessment Monitor FAM 10" approximately 1985, 2 pages, UK.

Gambro, "Fistula Assessment Monitor FAM 10 Operator's manual", approximately 1985, p. 1-17, UK.

Gambro, "Fistula Assessment Monitor FAM 10 Service manual", approximately 1985, p. 1-16, Sidcup Kent, UK.

J.S. Gani et al., "Use of the Fistula Assessment Monitor to Detect Stenoses in Access Fistulae", (abstract) Australian Society of Nephrology, 1989, p. 303-306, Australia.

Jonathan S. Gani, "Use of the Fistula Assessment Monitor to Detect Stenoses in Access Fistulae", American Journal of Kidney Diseases, vol. XVII, No. 3, pp. 303-306, Mar. 1991, Newcastle, Australia.

RN Greenwood et al., "Assessment of Arteriovenous Fistulae From pressure and Recirculation Studies Clinical Experience in 186 Fistulae", Abstract p. 106, 1985, London, UK.

RN Greenwood et al., "Assessment of Arteriovenous Fistulae From pressure and Recirculation Studies. Clinical Experience in 215 Upper Limb Fistulas", EDTA-ERA, vol. 22, pp. 296-302, 1985 London, UK.

RN Greenwood et al., "Assessment of Arteriovenous Fistulae From pressure and Thermal Dilution Studies. Clinical Experience in Forearm Fistulae", Clinical Nephrology, vol. 23, No. 4, pp. 189-197, 1985 UK.

L. Goldstein et al., "The Assessment of Arteriovenous Fistulae From P pressure and Recirculation Studies", Porc EDTA-ERCA, vol. 14, pp. 207-215, 1985 UK.

Lynn W. Hart et al., "A non Invasive Electromagnetic conductivity Sensor for Biomedical Applications", IEEE Transactions on Biomedical Engineering, vol. 35, No. 12, pp. 1011-1022, Dec. 1988, Maryland.

Robert L. Hester "The Determination of Hemodialysis Blood Recirculation Using Blood Urea Nitrogen Measurements" American Journal of kidney Diseases, vol. XX, No. 6, pp. 598-602, Dec. 1992, Mississippi.

M. Kramer et al., "Automated measurement of Recirculation", EDTA-ERCA, Journal, vol. XIX, No. 2 Apr. 1993, p. 6-9.

Matthias Kramer et al., "A Device for Control of Thermal Parameters and Recirculation Measurement in Hemodialisys", Nov. 1992, 15 pages, Germany.

Transonic Systems, Inc., "Transonic Hemodialysis Monitor Measure Access Flow Recirculation Cardiac Output Routinely during Dialysis", Apr. 1995 EDTA-ERCA, 2 pages.

Nikolai M. Krivitski, "Novel Method to Measure Access Flow during Hemodialysis by Ultrasound Velocity Dilution Technique", Jul. 27, 1995, ASAIO Journal, pp. 0014-0018.

Thomas A Depner and Nikolai M. Krivitski, "Clinical Measurement of Blood Flow in Hemodialysis Access Fistulae and Grafts by Ultrasound Dilution", Jul. 27, 1995, ASAIO Journal, pp. 0018-0022.

Thomas A Depner et al. "Hemodialysis Access Recirculation Measured by Ultrasound Dilution", Jul. 27, 1995, ASAIO Journal, pp. 0022-0026.

Nikolai M. Krivitski, "Novel Method to Measure Access Flow during Hemodialysis by Ultrasound Dilution (UD)", 1995, ASAIO Journal, pp. M741-M745.

Nikolai M. Krivitski, "Theory and Validation of Access Flow Measurement by Dilution Technique during Hemodialysis", Kidney International vol. 48 (1985), pp. 244-250.

Nikolai M. Krivitski, "Accuracy of Ultrasound Dilution Method to Measure Access Flow during Hemodialysis", XIIIth International Congress of Nephrology, Abstract, 1995, p. 488.

Nikolai M. Krivitski, "New Method to Measure Recirculation (RC) and Access Flow during Hemodialysis", American Nephrology Nurses Assosiation 26th National Symposium Exhibitor Continuing Education Program, Abstract 1995, 1 page.

T. Depner, "Changes in Access Blood Flow (Qac) and Appearance of Recirculation (RC) during Hemodialysis", XIIIth International Congress of Nephrology, Abstract, 1995, p. 570.

T. Depner et al. "Hemodialysis Access Recirculation Measured by Ultrasound Dilution", Abstract, Supplement to Jan.-Mar. 1995, ASAIO Journal, vol. 41, No. 1, p. 80.

T. Depner and Nikolai M. Krivitski, "Clinical Measurement of Blood Flow in Hemodialysis Access Fistulae and Grafts by Ultrasound Dilution", 1995, ASAIO Journal, Abstracts, Supplement to Jan.-Mar., vol. 41, No. 1, p. 80.

Transonic Systems, Inc.,"Recirculation, Access Flow Measurement" 1995, pp. 19-26.

Nikolai M. Krivitski, "Cardiac Output Measurement in Extracorporeal Systems by Ultrasound Velocity Dilution", ASAIO Journal, Abstracts, 1995, p. 82.

Jeffrey Sands et al., "The effect of Doppler Flow Screening Studies and Elective Revisions on Dialysis Access Failure", Reprint from ASAIO Transactions, Jul.-Sep. 1992, pp. M524-M527.

John L. Nosher, "Death Taxes and Vascular Access Dysfunction, Seminars in Dialysis", vol. 4, No. 2, pp. 67-68, Apr.-Jun. 1991, New Jersey.

In-line Diagnostics (brochure) "Non Invasive Blood Volume Monitoring", two pages, 1994.

John D. Bower and Thomas G. Coleman, "Circulatory Function During Chronic Hemodialysis", vol. XV Trans. Amer. Soc. Artif. Int. Organs, 1969, pp. 373-377.

C. Aldridge, "The Use and management of Arteriovenous Fistulae Fact and Fiction", EDTNA ERCA, Journal SVII-4, pp. 29-35, Oct. 1991, United Kingdom.

R.L. Hester et al., "Non Invasive Determination of Recirculation in Dialysis Patient on Dialysis", ASAIO Journal, pp. M190-M193, 1992, Mississippi.

R.L. Hester et al., "Non Invasive Measurement of Recirculation in Dialysis in Dialysis Patient", Abstract No. 7, Jul. 1992, one page.

R.N. Greenwood and W.R. Cattell, "Single Needle Dialysis", Journal of Medical Engineering & Technology, vol. 6, No. 3 (May/Jun. 1982), pp. 93-98.

K. Konner, H M Karnahl, "Transvenous Serial Xero-Arteriographic Method for AV-Fistulas in Haemodialysis Patients", Proc EDTA (1981), vol. 18, pp. 305-309.

L. Forsberg, T.Holmin and E. Linstedt, "Quantitative Doppler and Ultrasound Measurements in Surgically Performed Arteriovenous Fistulas of the Arm.", Acta Radiologica Diagnosis 21 (1980), Fasc. 6, pp. 769-771.

Schneditz et al "Cardiopulmonary recirculation in Dialysis", ASAIO Journal, 1992, pp. M194-M196.

Guyton "Textbook of Medical Physiology", 1991, pp. 287-288.

Gothlin et al., "A Dye-dilution method for the determination of blood flow in Cimino Brescia Arterio-venous Fistulae", Investigative Urology—The Williams and Wilkins Co—1977, pp. 167-168.

Louk et al., "Magnetic Resonance, a new method for measuring blood flow haemodialisys fistulae", Kidney international, vol. 45 (1994), pp. 884-889.

Rocha et al., Arterio-venous Shunt Measured by Dye Dilution . . . and Cardivascular Diagnosis, 11, pp. 437-481 (1985).

Gottlieb et al., "Radiotracer Method for non Surgical Measurement of Blood Flow in Bovine graft AV Fistulas"—Dialysis Transplantation Forum (1976), pp. 107-108.

Lantz "Determination of Blood Flow trough AV Fistulae and Shunts", Acta Radiologica Diagnosis 20 (1979), vol. 5, pp. 727-736.

Depner et al. 'Access flow measurement from recirculation of urea during hemodialysis during reversed bloodlines'—J. Am Soc Nephrol, vol. 6, 1995, p. 486.

Lindsay. R. M. et al. 'Monitoring vascular access flow'—Advances in Renal replacement therapy, vol. 6, No. 3, 1999, pp. 273-277.

Lindsay. R. M. et al. 'The estimation of hemodialysis blood flow rates by a urea method is a poor predictor of access outcome' Asaio J. vol. 44, 1988, pp. 818-822.

Sternby, J. "Urea sensors—A world of possibilities"—Advances in Renal replacement therapy, vol. 6, No. 3, 1999, pp. 265-272.

Yarar, D. et al. Ultrafiltratio method for measuring vascular access flow rates during hemodialysis >>, Kidney International, vol. 56, No. 3, 1999, pp. 1129-1135.

Polaschegg et al. "On-line Dynamic Measurement of Fistula Pressure during Haemodialysis for Detection of Access Stenosis and Bad Needle Placement", XXVIth Conference EDTNA-ERCA, Prague, Jul. 5-8, 1997, p. 23.

Polaschegg et al. "Dynamic Pressure Measurement for Detection of Blood Access Stenosis", EDTNA-ERCA Journal, 1998, XXIV 4, pp. 39-44.

Polaschegg et al. "Pressure Drops in Cannulas for Hemodialysis", The International Journal of Artificial Organs, vol. 24, No. 9, 2001 / pp. 614-623.

Lodi et al. "A Novel Model-Based Method for Monitoring the Hemodialysis Vascular Access", The 2001 ASN/ISN World Congress of Nephrology, Codes: FC—Free Communication; PS—Poster Session, 294A-A1513, pp. 294A-295A.

Stanley Frinak et al. << Dynamic Venous Access Pressure Ratio Test for Hemodialysis Access Monitoring >>, American Journal of Kidney Diseases, vol. 40, No. 4 Oct. 2002, pp. 760-768.

Anatole Besarab et al. "Utility of Intra-Access Pressure Monitoring in Detecting and Correcting Venous Outlet Stenoses Prior to Thrombosis", Kidney International, vol. 47 (1995), pp. 1364-1373.

Anatole Besarab et al. "Effects of Systemic Hemodynamics on Flow within Vascular Accesses Used for Hemodialysis", ASAIO Journal 2001, vol. 47, pp. 501-506.

W. Kleinekofort et al. "Extracorporeal Pressure Monitoring and the Detection of Vascular Access Stenosis", The International Journal of Artificial Organs, vol. 25 / No. 1, 2002 / pp. 45-50.

Anatole Besarab et al. "Detection of Access Strictures and Outlet Stenoses in Vascular Accesses—Which test is best?", ASAIO J, vol. 43: pp. M543-M547, 1997.

Anatole Besarab et al. "Simplied Measurement of Intra-Access Pressure", Journal of the American Society of Nephronology, copyright 1998 by the American Society of Nephrology, vol. 9: pp. 284-289.

International Search Report for PCT/IB2005/001347, dated Jan. 4, 2006.

In-line Diagnostics (brochure) "Improve the Clinical Outcome of Every Patient", four pages, at least as early as Apr. 7, 2004.

In-line Diagnostics (brochure) "The Crit-Line System", two pages, at least as early as Apr. 7, 2004.

* cited by examiner

APPARATUS FOR CONTROLLING BLOOD FLOW IN AN EXTRACORPOREAL CIRCUIT

TECHNICAL FIELD

The invention relates to an apparatus for controlling blood flow in an extracorporeal circuit. In particular, the apparatus of the invention is destined to operate in extracorporeal circuits of machines for blood treatment such as, for example, machines for hemodialysis, hemofiltration, hemodiafiltration or plasmapheresis.

BACKGROUND ART

Machines for treatments such as the ones described above are used for operating blood treatment processes in patients suffering from partial or total kidney failure. Blood treatment apparatus typically comprise an extracorporeal circuit which is provided with at least one blood treatment unit, as well as at least one access branch destined to connect a blood removal zone with a first chamber of the treatment unit; the extracorporeal circuit also comprises a second branch i.e. a blood return branch which develops downstream of the treatment unit from the first chamber, towards a blood return zone to the patient.

There is usually a peristaltic pump located at the access branch, which pump is destined to act on the access branch in order progressively to move the blood flow towards the treatment unit.

Independently of the type of treatment to be performed on the patient, a precise knowledge of the quantity of blood taken from the patient is of maximum importance, being also the quantity treated by the machine the extracorporeal blood circuit is connected to.

It is important to note that the blood flow which can be obtained through the use of peristaltic pumps depends on various factors, mainly:

the geometry and material of the particular tract of blood line to which the peristaltic pump is associated;
the geometry of the pump rotor, as well as the angular velocity of the peristaltic pump;
the geometry of the tract of tubing upstream of the pump, and the access organ used for removing blood from the patient;
the pressure existing, in particular, in the tracts of tubing upstream and downstream of the peristaltic pump;
the physical-chemical characteristics of the blood.

In a first prior-art solution used in the past, the flow produced by the peristaltic pump was considered proportional, through a special conversion factor, to the instant angular velocity of the pump itself.

In other words, in order to obtain a theoretical flow value through the pump segment, the angular velocity of the pump was multiplied by a constant calibration factor. The theoretical flow value obtained could be viewed on a display on the machine, or not as the case required.

However, considering the numerous factors briefly mentioned above that influence the entity of the flow really provided by the peristaltic pump, it is easy to see how a flow calculation using a simple proportional factor for the angular velocity is affected by errors which cannot be viewed as irrelevant. With this aim, i.e. to realise an apparatus for blood treatment in which a flow value through the pump tract of the extracorporeal circuit as close as possible to reality were known, U.S. Pat. No. 5,733,257 describes a calibration process for a peristaltic pump destined to be used with an apparatus internally provided with at least a flow meter. The process involves introducing a fluid into the pump tubing segment and activating the peristaltic pump at a constant revolution count. Once regularly revolving at the determined velocity, the pressure upstream of the pump tubing segment is read, as is the fluid flow effectively crossing the pump tract, using the flow meter internal of the machine, and in this way a pair of calibration readings is obtained (effective flow, arterial pressure) according to the pre-selected angular velocity of the pump.

The above-described process is repeated, varying the arterial pressure upstream of the pump, so as to obtain various arterial pressure-effective flow pair readings for a same angular velocity. At this point a calibration curve is calculated, thanks to which a pressure-effective flow relation is created for the selected angular velocity. By repeating the above-described calibration criteria over a range of angular velocities, a calibration curve set is created. When the machine is started up, the calibration curves are used to calculate the effective flow of the peristaltic pump on the basis of the known and measured values of the pump angular velocity and the pressure level in the tube tract upstream of the pump.

A further process for determining and controlling the blood flow is described in patent WO03/055542. This process involves determining a function of calibration F in the following variables:

v1 in relation to the angular velocity of the pump ($\omega$),
v2 in relation to the arterial pressure (Part) in the portion of the access branch upstream of the peristaltic pump
v3 in relation to an effective blood flow (Qactual) crossing the access branch
v4 in relation to the time that has passed since start of treatment
v5, in relation to the geometrical characteristics of an access organ which is operatively couplable to the extracorporeal circuit;
v6, in relation to the length of the tract of tube of the access branch upstream of the peristaltic pump.

The process periodically calculates the effective flow Qactual thanks to this function and, as it knows the variables from v1 to v6, the process if necessary modifies, at time intervals, the angular velocity of the peristaltic pump if the difference (Qactual−Qset) between effective flow and desired flow is out of a prefixed interval.

SUMMARY OF THE INVENTION

Although the above-described system offers the possibility of controlling the angular velocity of the peristaltic pump so as to cause the real flow generated thereby to converge with the desired flow, it requires that at each control interval the mentioned parameters be measured, the corresponding real flow calculated and continual corrective operation performed on the angular velocity of the blood pump.

The Applicant therefore set himself the problem of providing a technical solution which would determine the real flow provided by the peristaltic pump a priori, and therefore control the pump with no need for a timed control, nor for periodical measuring of the pressure and as a consequence making continual variations in the angular velocity of the pump. At the same time, an aim of the invention is to provide a technical solution which reaches a high level of accuracy.

A further aim of the invention is to provide a technical solution which enables a prior forecast, for example at start of treatment, blood pump operating conditions which are incompatible with set safety margins.

In particular, an auxiliary aim of the invention is to provide a system which advises the operator if the prescription for the desired blood flow can lead to situations which might be dangerous in the patient's blood removal zone.

These and other aims besides, which will better emerge during the following description, are substantially attained by an apparatus for control of blood flow in an extracorporeal blood circuit, as it is described in claim 1.

Further characteristics and advantages will better emerge from the following description in relation to some preferred but non-exclusive embodiments of an apparatus for control of blood flow in an extracorporeal blood circuit according to the invention.

SHORT DESCRIPTION OF THE DRAWINGS

The description will be made with reference to the figures of the accompanying drawings, provided by way of non-limiting example, in which.

DETAILED DESCRIPTION

Figure 1:
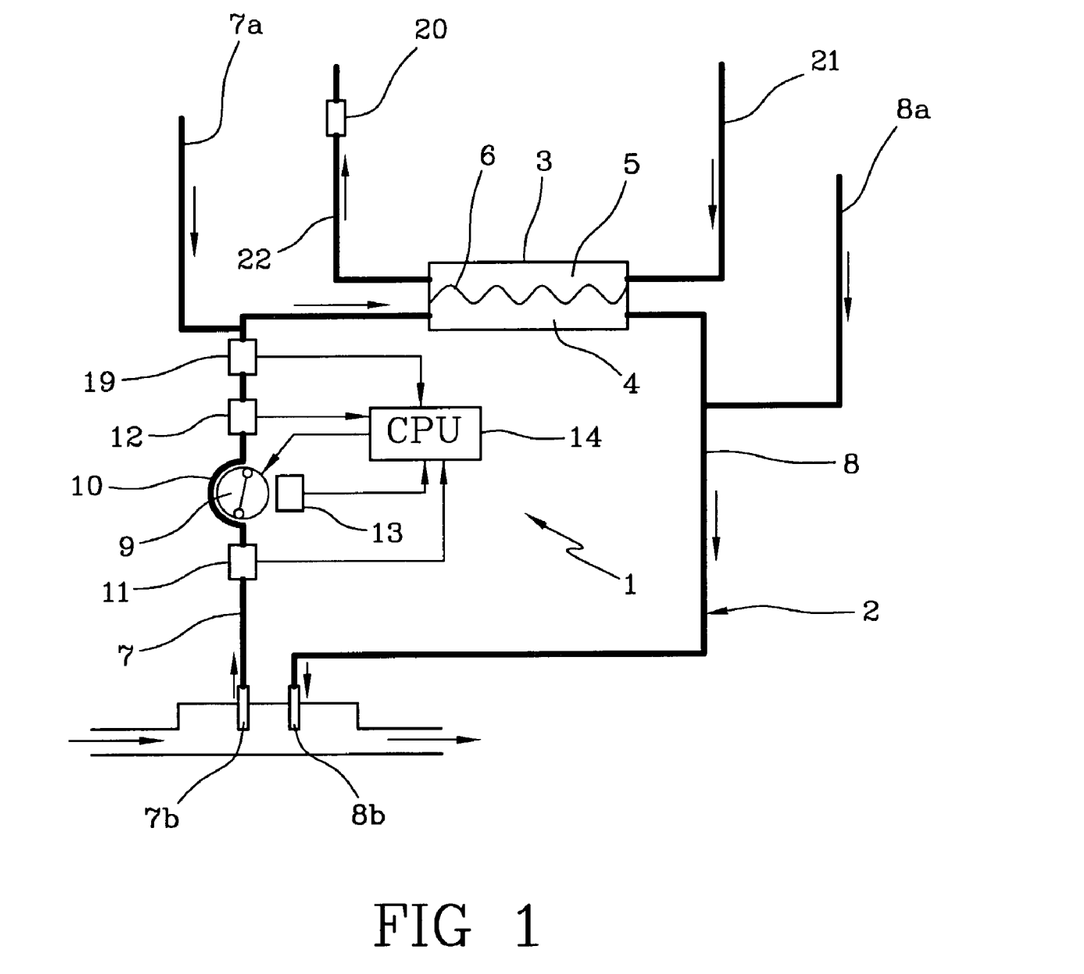
FIG. 1 is a schematic representation of a machine for blood treatment in which the apparatus for control of blood flow of the invention can operate.
Figure 2:
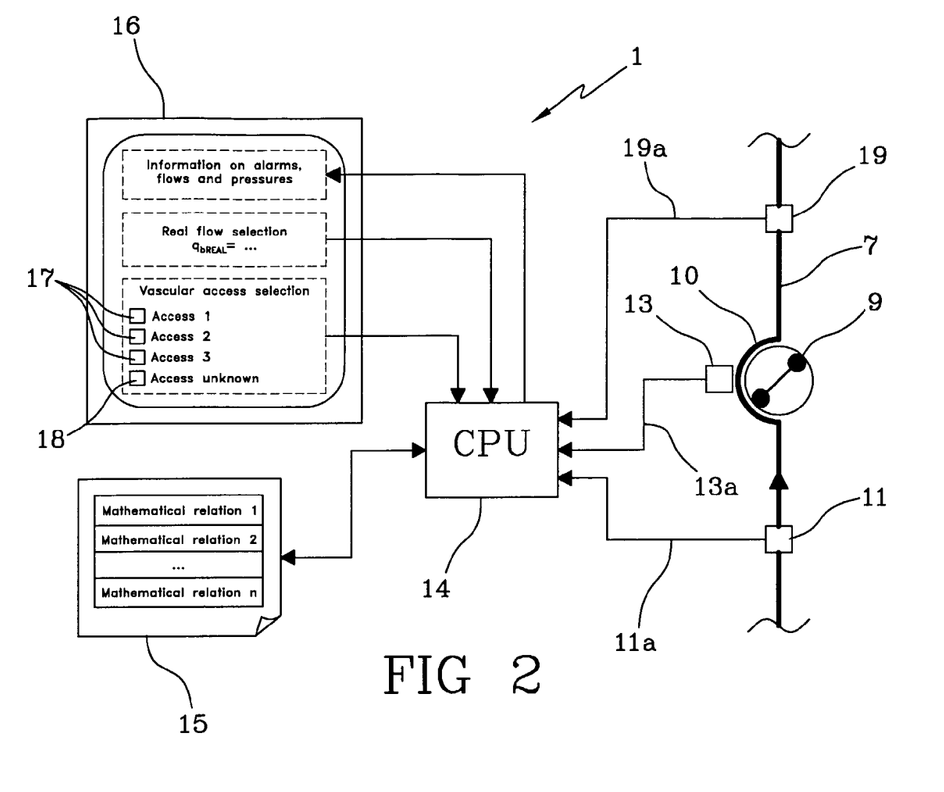
FIG. 2 is a block diagram illustrating an embodiment of the apparatus for control of blood flow of the present invention in an extracorporeal blood circuit.
Figure 3:
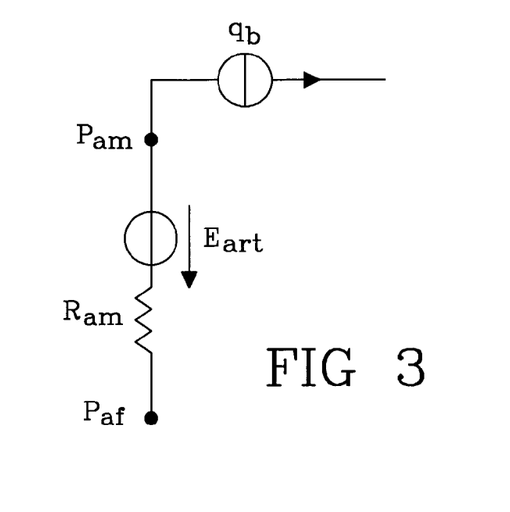
FIG. 3 is a schematic diagram of an electrical circuit equal to a part of the blood circuit in which the apparatus of the invention can operate.

With reference to the figures of the drawings, 1 denotes in its entirety an apparatus for control of blood flow in an extracorporeal blood circuit, denoted by 2 in the figures. The extracorporeal blood circuit 2 can be, for example, used for performing the extracorporeal blood circulation in a machine for blood treatment of a patient, for example a machine for hemodialysis and/or hemofiltration and/or ultrafiltration and/or hemodiafiltration and/or plasmapheresis, or for any other combination of the above-listed treatments. Obviously the extracorporeal circuit can also be used in apparatus destined for other treatments not expressly mentioned herein, where an extracorporeal blood circulation is required.

The extracorporeal circuit 2 usually comprises at least a first chamber 4 of a blood treatment unit 3 having at least a second chamber 5, separated from the first chamber by a semi-permeable membrane 6. At least one access branch 7 extends between a blood removal zone from a patient or donor and the first chamber of the treatment unit 4; at least a return branch 8 extends downstream of the treatment unit, between the first chamber 4 and a return zone of the blood to the patient; a peristaltic pump 9 is operatively associated to a length of pump tube 10 of the extracorporeal circuit access branch. Usually, at the removal and return branches of the blood to or from the patient, access means 7b, 8b are provided to the cardiovascular system of the patient, for example constituted by needles of appropriate sizes, from catheters or accesses of different types. The second chamber 3 of the unit can be, for example, connected to a device (not shown in the detail) which can send a dialysis liquid towards the second chamber and evacuate from the second chamber a dialysed liquid in which waste products have been accumulated together with excess of water from the blood. Similarly one or more liquid infusion lines can be provided (for example 7a and 8a), connected at one end to an infusion liquid source (a bag or in-line infusion liquid preparation system) and at the other end to the extracorporeal circuit, or directly to the patient or donor.

The blood flow control apparatus 1 has at least one sensor 11, located on the access branch, in a portion of the access branch which is upstream of the peristaltic pump 9, in order to read an arterial pressure ($P_{am}$) and generate a respective signal 11a in output which is proportional to the arterial pressure. The first pressure sensor 11 operates immediately upstream of the peristaltic pump and is able to detect the pressure in the tract of tubing interpositioned between the blood removal zone from the patient and the peristaltic pump 9. In this tract of tubing the pressure is usually negative in relation to atmospheric pressure.

The blood flow control apparatus 1 can include a sensor 12, located in the access branch, in a portion of the branch which is downstream of the peristaltic pump 9. The pressure sensor 12 is able to read the pressure in the tract of tubing interpositioned between the peristaltic pump 9 and the unit 3 and sends a corresponding signal 12a to the unit 3. There is usually a positive pressure in this tract of tubing in relation to atmospheric pressure.

The apparatus 1 also comprises a sensor 13, operatively associated to the peristaltic pump 9 and predisposed to read an angular velocity ω (omega) of the pump and to generate a corresponding output signal 13a, indicating the rotation velocity of the peristaltic pump. The above-described sensors are operatively connected with a control unit 14 to which the sensors send respective signals.

The control unit is provided with a memory indicated with 15 in the attached drawings. The memory 15 records a plurality of mathematical relations, each of which exhibits a respective and different mathematical expression which is a function of the vascular access organ. In other words, the memory 15 includes mathematical functions, pre-loaded or loadable by the user, each of which is characteristic of a respective vascular access and each of which mathematically links, in a definite and univocal manner, the blood flow crossing the access branch with the angular velocity of the peristaltic pump.

The apparatus 1 also includes a user interface 16 for enabling the setting of a desired value of the blood flow ($q_{bREAL}$) crossing the access branch and for enabling an insertion of at least one datum relating to the vascular access, which access is to be used during the treatment. The interface can be of various types. For example, it can comprise a touch screen in which special needle selection fields 17 appear, enabling the user to select the type of needle to be used in the treatment. Alternatively, user interfaces including a keyboard and non-touch monitor systems can be used. Also, codified data carried by the vascular access or the vascular access packaging can be used (e.g. in the form of a bar code or colour codes or data banks with wireless data transmission), which can be read off by special sensors integrated into the user interface.

The control unit is connected to the user interface with the peristaltic pump and the memory and is programmed to perform a process comprising the following stages.

1. identification of the vascular access;

2. selection (from among the plurality of mathematical relations in the memory) of the relation corresponding to the identified vascular access;

3. calculation, using the mathematical relation loaded from the memory, of at least one or both the following values:

a value at which the angular velocity of the peristaltic pump is to be set, as a function of the set value for the desired flow ($q_{bREAL}$), and a theoretical value of the arterial pressure in the tract of arterial branch upstream of the peristaltic pump, as a mathematical function of the set value for the desired flow ($q_{bREAL}$).

The user interface enables insertion of an identification datum of the vascular access, and the control unit 14 associates to that vascular access identity datum the respective among the plurality of mathematical relations, i.e. the relation which best describes the behaviour of the access on variation of the flow crossing it.

If the user does not know or is unable to identify the vascular access identification to be used, the user interface enables insertion of a datum which will indicate that the user does not know the identity of the vascular access (for example, by use of a field 18 in the interface itself). In this case the control unit activates a corresponding automatic identification procedure of the vascular access, comprising at least the following stages:

applying a variation in angular velocity on the peristaltic pump;

determining a plurality of corresponding real values relating to the pressure upstream of the peristaltic pump, each being relative to a respective angular velocity value of the pump;

identifying, thanks to the real pressure values, the mathematical function corresponding to the vascular access used.

In other words, by recording the pressure (read by the sensor 11) at various flow velocities it is possible to recognise which of the mathematical functions present in the memory 15 best describes the vascular access in use.

In greater detail, each of the mathematical relations stored in the memory 15 can in reality can comprise two relations: a first one which enables a mathematical calculation of a theoretical arterial pressure value upstream of the peristaltic pump, as a mathematical function of the set value for the desired flow ($q_{bREAL}$), and a second mathematical relation which enables a mathematical calculation of the value at which the peristaltic pump angular velocity can be set as a function of the theoretical value of the arterial pressure. In a preferred embodiment the first mathematical relation calculates the theoretical value of the arterial pressure in the arterial branch upstream of the peristaltic pump as a mathematical function of both the set value for the desired flow ($q_{bREAL}$) and of the value of at least one parameter relating to the chemical/physical values of the patient's blood. This parameter, for example, might relate to the viscosity of the patient's blood, and can comprise the hematocrit of the patient's blood.

The hematocrit value can be known or, if not, can be determined by special means acting on the extracorporeal circuit or on the dialysis side, and connected to the control unit. The means for calculating the patient's blood hematocrit comprise means for determining the hematic concentration of hemoglobin and means for estimating sodium plasma concentration. The control unit is connected to the means and estimates the hematocrit value starting from the hematic concentration of hemoglobin and the plasma concentration of the sodium.

In order to calculate the hematocrit concentration of hemoglobin the means comprise, for example, a known optical device 19, of the type bearing the mark Hemoscan®, manufactured by Gambro Dasco SpA operating on the arterial branch of the extracorporeal circulation.

In order to calculate the sodium plasma concentration, the means comprise a device marketed with the mark Diascan® and manufactured by Gambro Dasco SpA; this device uses the data on the conductivity or concentration of the fresh dialysis liquid in the inlet conduit 21 and a conductivity or concentration sensor 20 operating on the used liquid discharge conduit 22 connected to the second chamber 5 of the treatment unit 3. By creating a concentration or conductivity change in the dialysis liquid upstream of the unit 3 and analysing the corresponding change of concentration or conductivity downstream, the sodium clearance can be calculated, as can the plasma concentration of sodium, as described for example in European Patents nos. EP547025, EP658352 and EP920877, incorporated with the present for reference purposes.

The invention can also include a correction of the angular velocity of the pump during the treatment, to take into account any changes in patient parameters. To this end the control unit 14 periodically checks, during the extracorporeal treatment, the value of the parameter relating to the chemical/physical characteristics of the patient's blood and mathematically re-calculates corresponding theoretical values of the arterial pressure in the arterial branch upstream of the peristaltic pump as a mathematical function of the set value for the desired flow ($q_{bREAL}$) and, successively, the value of the parameter. Correspondingly the unit 14 can re-calculate and set, on the pump, the angular velocity value needed in order to obtain the desired flow at the new arterial pressure value.

Note that, independently of how it calculates the angular velocity, the control unit also sets the angular velocity of the pump on the basis of the calculated value.

Since, according to one aspect of the present invention, the unit 14 determines the theoretical value of the arterial pressure in the arterial branch upstream of the peristaltic pump as a mathematical function of the set value for the desired flow ($q_{bREAL}$), it can also be programmed to compare the calculated value with an "acceptability interval". In this case, following comparison, two different situations might be presented. In particular, the control unit is predisposed to signal whether the theoretical value of the arterial pressure is below a predetermined threshold, and to calculate, using the mathematical relation, the angular velocity of the peristaltic pump and the real flow corresponding to an arterial pressure that is equal to the prefixed threshold. Should, following this comparison, the control unit have ascertained that the theoretical value of the arterial pressure is above a prefixed threshold, the unit can calculate the limit angular velocity of the peristaltic pump and the limit real flow corresponding to the prefixed pressure threshold. In the latter case the control unit is predisposed to transmit to the user interface and visualize thereon the limit real flow value reachable without falling below the prefixed arterial pressure threshold.

The invention also concerns a software program comprising instructions for enabling the control unit to perform the various stages of the described process of identification of the vascular access, a calculation of the arterial pressure, a calculation and setting of the angular velocity of the pump, a control of respect for the range of arterial pressure and correction thereof in cases of variations in one or more of the patient parameters. The program in question can be memorised on a support chosen from a group containing:

a magnetic recording support, an optical recording support, a RAM memory, an electrical carrier signal, an electromagnetic carrier signal, a ROM memory.

In a preferred embodiment, the instructions constituting the program are stored in a mass memory associated to the apparatus and, following activation of the apparatus, the instructions are loaded in the RAM memory 15 in order to be available to the control unit, which can be, for example, a microprocessor.

The invention also comprises a machine for blood treatment which is capable of performing one or more of the following treatments:
hemodialysis,
hemofiltration,
hemodiafiltration,
pure ultrafiltration,
plasmapheresis
and is also provided with an apparatus for controlling the blood flow in an extracorporeal blood circuit as described and illustrated in the accompanying figures of the drawings.

EXAMPLES OF SOME PREFERRED EMBODIMENTS OF THE INVENTION

The calculation of the angular velocity of the peristaltic pump for obtaining the desired blood flow in the extracorporeal circuit is based on the following relations:

$$\omega = f(q_{bREAL}, P_{am}) \tag{E1}$$

which express the dependence of the real blood flow $q_{bREAL}$ on the angular velocity of the pump and on the pressure measured in the arterial branch of the extracorporeal circulation $P_{am}$.

$$P_{am} = g(q_{bREAL}, \text{needle, blood, vascularaccess, extracorporealcircuit}) \tag{E2}$$

which links $P_{am}$ to known $q_{bREAL}$ the type of vascular access and/or needle used, the patient's blood characteristics and the extracorporeal circuit characteristics.

(E2), substituted by (E1), enables an expression of the angular velocity, according to the only desired $q_{bREAL}$ and thus the following problem can be analytically resolved:

$$\omega = h(q_{bREAL}) \tag{E3}$$

as for the (E1) relation, a possible valid representation is the following:

$$q_{bREAL} = a \cdot \omega + b \cdot \omega \cdot P_{am} + c \cdot P_{am} + d \tag{00}$$

from which we can obtain the following equation:

$$\omega = -\frac{-q_{bREAL} + c \cdot P_{am} + d}{a + b \cdot P_{am}} \tag{0}$$

which expresses the angular velocity according to the two values $q_{bREAL}$ and $P_{am}$.

The relation (E2) can be derived from the electrical analogue represented in FIG. 3.

In particular, we can write:

$$P_{af} - E_{art} - P_{am} = R_{am} \cdot q_{bREAL} \tag{1}$$

where $P_{af}$ is the intravascular pressure of the vascular access, $P_{am}$ is the pressure measured along the arterial branch of the extracorporeal circulation, and $E_{art}$ is the hydrostatic pressure due to the difference of level between the pressure sensor and the vascular access.

While values $P_{am}$ and $E_{art}$ are obtainable from the device managing the extracorporeal circulation and the pressure transducer position, the value of resistance $R_{am}$ can be found by obtaining the characteristics of the extracorporeal blood line and the blood circulating therein.

Supposing that a needle is used for connecting the extracorporeal circuit to the vascular access, a reasonable approach would be to assume that the whole drop in blood pressure would be concentrated along the needle itself. In this way the resistance $R_{am}$ is a function of the blood flow $q_b$, the viscosity of the blood (i.e. the hematocrit, Hct) and the geometrical properties of the needle, as follows:

$$R_{am} = R_{Poiseuille} \cdot f(q_b, Hct, \text{needle})$$

where $R_{Poiseuille}$ is the theoretical hydraulic resistance, calculated using Hagen-Poiseuille's law from the knowledge of the needle's geometry (internal diameter and length) and assuming a water viscosity at 20° C.

Experimental Determination of the Relation $f(q_b, Hct, \text{Needle})$

The relation $f(q_b, Hct, \text{needle})$ was found by ex-vivo experimentation, i.e. by measuring the drop in blood pressure along various types of needle having different blood flow and hematocrit values. The experimental points can be interpolated using a second and first degree equation with respect to the flow, found using the squared minima method:

$$f(q_b, Hct, \text{needle}) = \alpha_2 \cdot q_b^2 + \alpha_1 \cdot q_b + \beta \text{ or } f(q_b, Hct, \text{needle}) = \tilde{\alpha}_1 \cdot Hct \cdot q_b + \tilde{\alpha}_0$$

With a good degree of approximation, the parameters $\alpha_1$, $\alpha_2$, $\tilde{\alpha}_0$ and $\tilde{\alpha}_1$ are dependent only on the type of needle (i.e. on the geometry and flow direction), while the parameter $\beta$ depends on the type of needle and the hematocrit. In particular, two expressions for parameter $\beta$ were found, of first and second degree with respect to the hematocrit:

$$\alpha_2 = \alpha_2(\text{needle})$$

$$\alpha_1 = \alpha_1(\text{needle})$$

$$\tilde{\alpha}_1 = \tilde{\alpha}_1(\text{needle})$$

$$\tilde{\alpha}_0 = \tilde{\alpha}_0(\text{needle})$$

$$\beta = \beta_2(\text{needle}) \cdot Hct^2 + \beta_1(\text{needle}) \cdot Hct + \beta_0(\text{needle}) \text{ or } \beta = \beta_1(\text{needle}) \cdot Hct + \beta_0(\text{needle})$$

In conclusion, the hydraulic resistance to the extracorporeal circulation can be expressed as:

$$R_{am}() = R_{Poiseuille} \cdot (\alpha_2 \cdot q_b^2 + \alpha_1 \cdot q_b + \beta_2 \cdot Hct^2 + \beta_1 \cdot Hct + \beta_0)$$

The experimental characterisation was performed for the following value intervals:

Blood flow: from 0 to 500 ml/min hematocrit: from 30 to 45% needle type: 15, 16, 17 Gauges at 28 and 33 mm nominal length.

From the expression of $R_{am}()$ found and from equation (1), expression (E2) can be obtained for the arterial pressure as a function of the real blood flow and the physical-geometrical characteristics of the needle, the blood, the vascular access and the extracorporeal circuit:

$$P_{am} = P_{af} - E_{art} - R_{am}() \cdot q_{bREAL} =$$
$$= g(q_{bREAL}, \text{needle, blood,}$$
$$\text{vascularaccess, extracorporealcircuit})$$

This expression, placed in equation (0), enables finding the expression (E3) of the angular velocity of the blood pump Co which enables obtaining the effective selected blood pump flow $q_{bREAL}$.

Below the steps for finding the angular velocity are described:

supposing intra-vascular pressure at vascular access to be $P_{af}$ and with hydrostatic pressure $E_{art}$ constant for the whole duration of the dialysis treatment;

in the conditions reported in the following table.

| Condition | Hct(0) (initial hematocrit) | Type of needle/vascular access |
|---|---|---|
| CASE 1 | KNOWN | KNOWN |
| CASE 2 | UNKNOWN | KNOWN |
| CASE 3 | KNOWN | UNKNOWN (previously characterised) |
| CASE 4 | UNKNOWN | UNKNOWN (previously characterised) |
| CASE 5 | UNKNOWN | UNKNOWN |
| CASE 6 | KNOWN | UNKNOWN |

When relation (E2) has been found it is possible to determine the arterial pressure $P_{amT}$ corresponding to the desired value of blood flow $q_{bREAL}$.

Thus a check can be made on the value obtained for arterial pressure $P_{amT}$, to verify that it is not too negative and therefore damaging to the fistula (SAVE FISTULA FUNCTION.)

If the arterial pressure $P_{amT}$ obtained is above a previously-fixed (and therefore acceptable) threshold value (negative) $P_{amMIN}$ we can replace its value in the equation (0) in order to find the angular velocity (OT that makes reaching the target for real blood flow possible.

If the arterial pressure is below the threshold value (negative), a minimum arterial pressure value is imposed $\overline{P}_{amT}$ and the new target value for the real blood flow is found $\overline{q}_{bT}$, thus resolving the equation (E2).

Then the above is expressed using a mathematical formalism:

If $P_{amT} > P_{amMIN}$

Then $$\omega_T = f(q_{bT}) = -\frac{-q_{bT} + c \cdot P_{amT} + d}{a + b \cdot P_{amT}}$$

Otherwise $$\overline{P}_{amT} = P_{amMIN} + k_{saftey} \Rightarrow \overline{q}_{bT}(from\ equation\ E2) \Rightarrow \overline{\omega}_T$$
$$= f(\overline{q}_{bT})$$
$$= -\frac{-\overline{q}_{bT} + c \cdot \overline{P}_{amT} + d}{a + b \cdot \overline{P}_{amT}}$$

| CASE 1 | | |
|---|---|---|
| Condition | Hct(0) (initial hematocrit) | Type of needle/vascular access |
| CASE 1 | KNOWN | KNOWN |

Let the initial hematocrit Hct(0) and the type of needle (or vascular access) be known.

Follow the steps beneath:

1.1) Blood pump stationary ($\omega=0$)

Rewriting equation (1) we have:

$$P_{af}(0) - E_{art} - P_{am}(0) = 0 \Rightarrow P_{am}(0) = P_{af}(0) - E_{art}$$

1.2) Let us fix a target for the real blood flow $q_{bREAL} = q_{bT}$ and rewrite the equation (1) in the following form:

$$P_{am}(0) - P_{amT} = R_{am} \cdot q_{bT} = R_{Poiseuille} \cdot (\alpha_2 \cdot q_{bT}^2 + \alpha_1 \cdot q_{bT} + \tilde{\beta}_1 \cdot Hct(0) + \tilde{\beta}_0) \cdot q_{bT}$$

from which we can find a value for $P_{am}$ that corresponds to the target value for the real blood flow $q_{bT}$:

$$P_{amT} = P_{am}(0) - R_{Poiseuille}(\alpha_2 \cdot q_{bT}^2 + \alpha_1 \cdot q_{bT} + \tilde{\beta}_1 \cdot Hct(0) + \tilde{\beta}_0) \cdot q_{bT} \quad (2)$$

1.3) SAVE FISTULA Function (as above described)

1.4) The angular velocity value can be adapted during treatment, following a variation in the patient's parameters, in such a way as to guarantee maintenance of the limits around the desired blood flow value.

In particular, variation in the patient's hematocrit is dealt with herein below. Let us suppose we have available a system for measuring a chemical-physical dimension of the blood, whose variations can be placed in relation to the variations in hematocrit with respect to the initial value $\Delta Hct$ (e.g: HEMOSCAN (Gambro Dasco SpA) or other systems).

We can rewrite the equation (2) in correspondence to a variation in hematocrit:

$$\Delta P_{amT} = R_{Poiseuille} \cdot (\tilde{\beta}_1 \cdot \Delta Hct_0) \cdot q_{bT}$$

This enables us to find the new value of the arterial pressure:

$$P'_{amT} \rightarrow P_{amT} + \Delta P_{amT}$$

At this stage we proceed as in step 3), finding the new value for the angular velocity $\omega'_T$ which will lead to obtaining the target value on hematocrit variation, without exceeding the limit value for arterial pressure $P_{amMIN}$.

In particular, the variation in angular velocity corresponding to the variation in hematocrit is the following:

$$\Delta \omega_T = \omega'_T - \omega_T$$
$$= \Delta f(q_{bT})|_{P_{am}}$$
$$= -\frac{c \cdot \Delta P_{amT} \cdot (a + b \cdot P_{amT}) - (-q_{bT} + c \cdot P_{amT} + d) \cdot b \cdot \Delta P_{amT}}{(a + b \cdot P_{amT})^2}$$

| CASE 2 | | |
|---|---|---|
| Condition | Hct(0) (initial hematocrit) | Type of needle/vascular access |
| CASE 2 | UNKNOWN | KNOWN |

Let the type of needle (or vascular access) be known, but not the initial hematocrit value.

Follow the steps beneath:

2.1) as in 1.1).

2.2) Identification of the initial hematocrit.

Variations are made to the velocity of the blood pump (for example a graduated rise), the values of the arterial pressure $P_{ami}$ are taken and the values corresponding to the real blood flow $q_{bREALi}$ calculated from the equation (00).

Then equation 1) can be rewritten in the following form, for a generic value of velocity of the blood pump $\omega_i$:

$$P_{am}(0) - P_{ami} = R_{ami} \cdot q_{bREALi} = R_{Poiseuille} \cdot (\alpha_2 \cdot q_{bREAL}^2 + \alpha_1 \cdot q_{bREALi} + \tilde{\beta}_1 \cdot Hct_i + \tilde{\beta}_0) \cdot q_{bREALi}$$

this can be resolved with respect to the hematocrit, to obtain:

$$Hct_i = \left( \frac{P_{am}(0) - P_{ami}}{R_{Poiseuille} \cdot q_{bREALi}} - \alpha_2 \cdot q_{bREALi}^2 - \alpha_1 \cdot q_{bREALi} - \tilde{\beta}_0 \right) \cdot \frac{1}{\tilde{\beta}_1}$$

From this expression it is possible to calculate the hematocrit values for each set value and to estimate the initial hematocrit value Hct(0) by mathematical procedures, for example by calculating the mean value from the i measurements.

From here we can proceed as in 1.2) of CASE 1, i.e. fixing a target for the real blood flow $q_{bREAL} = q_{bT}$.

2.3) as 1.3).

2.4) as 1.4).

| CASE 3 | | |
|---|---|---|
| Condition | Hct(0) (initial hematocrit) | Type of needle/vascular access |
| CASE 3 | KNOWN | UNKNOWN (previously characterised) |

Let the initial hematocrit be known and let us suppose that we need to identify a type of needle (or vascular access), already previously characterised.

Let us proceed as follows:

3.1) as 1.1).

3.2) Recognising the type of needle (or vascular access).

Variations are made to the blood pump velocity (for example a graduated rise), the values of arterial pressure are measured $P_{ami}$ and the values of the real blood flow are determined $q_{bREALi}$ from equation (00).

We can rewrite equation 1) in the following form, for a generic blood pump velocity value $\omega_i$:

$$P_{am}(0) - P_{ami} = R_{ami} \cdot q_{bREALi}$$

Suppose to find the values of theoretical arterial resistance for each k type of needle (or vascular access) previously characterised:

$$\tilde{R}_{ami,k} = R_{Poiseuille,k} \cdot f(q_{bREALi}, Hct(0), ago_k)$$

We can recognise the needle by applying any one of the minimisation methods (e.g. squared minima, maximum similarity, etc.); the type of needle k recognised will be the one for which $$\tilde{R}_{ami,k} \cong R_{ami} \text{ for each value of i}$$

Now we can proceed as in 1.2) of CASE 1, i.e. fixing a target for the real blood flow $q_{bREAL} = q_{bT}$.

3.3) as 1.3).

3.4) as 1.4).

| CASE 4 | | |
|---|---|---|
| Condition | Hct(0) (initial hematocrit) | Type of needle/vascular access |
| CASE 4 | UNKNOWN | UNKNOWN (previously characterised) |

Let us suppose that we need to identify a type of needle (or vascular access), already previously characterised, without knowing the initial hematocrit value.

Let us proceed as follows:

4.1) as 1.1).

4.2) Assigning a first-attempt value to initial hematocrit.

Let us suppose that we have available a system for measuring a chemical-physical dimension of the blood, whose variations can be placed in relation to the hematocrit variations with respect to the initial value ΔHct. Let us further suppose that we know a relation between the absolute values of the dimensions measured and the hematocrit, so that we can estimate the latter:

$$Hct(0) = H\tilde{c}t(0)$$

The value of the hematocrit can be estimated from the plasmatic concentration values of hemoglobin Hgb(0), expressed in g/dl, and sodium [Na], expressed in mEq/l, for example according to the formula:

$$H\tilde{c}t(0) = 3 \cdot Hgb(0) - \left( \frac{[Na] - 137}{12} \right)$$

The hemoglobin value is measurable by a device such as HEMOSCAN, manufactured by Gambro Dasco SpA.

The sodium plasma concentration can be estimated starting from the plasma conductivity value estimated by apparatus such as DIASCAN, manufactured by Gambro Dasco SpA.

Now we can proceed as in 3.2) of CASE 3, i.e. by recognising the type of needle (or vascular access) starting from the estimated value $H\tilde{c}t(0)$, and thereafter as in 2.2) of CASE 2 in order to refine the estimation for the initial hematocrit value.

4.3) as 1.3).

4.4) as 1.4).

| CASE 5 | | |
|---|---|---|
| Condition | Hct(0) (initial hematocrit) | Type of needle/vascular access |
| CASE 5 | UNKNOWN | UNKNOWN |

Let us suppose that we do not know the needle (or vascular access) type, nor can we associate it to any previously known type; also let us suppose we do not know the initial hematocrit value.

Let us proceed as follows:

5.1) as 1.1).

5.2) as follows:

5.2.1) Assignation of an estimated value for the initial hematocrit (as in 4.2) of CASE 4.

5.2.2) Identification of the type of needle (or vascular access).

Variations in blood pump velocity are made and the values of the arterial pressure taken; the values of the real blood flow are calculated using equation (00).

We can rewrite equation 1) in the following form, with a generic blood pump velocity $\omega_i$:

$$P_{am}(0)-P_{ami}=R_{ami} \cdot q_{bREAL}=R_{Poiseuille} \cdot (\tilde{\alpha}_1 \cdot H\tilde{c}t(0) \cdot q_{bREALi}+\tilde{\alpha}_0) \cdot q_{bREALi}$$

At this point, by applying any known parametric identification methods, the two unknown parameters can be found (angular coefficient and original ordinate $R_{Poiseuille} \cdot \tilde{\alpha}_1$ e $R_{Poiseuille} \cdot \tilde{\alpha}_0$) which describe the vascular access on variation of the blood flow and the hematocrit.

Then we can proceed as in 1.2) of CASE 1, i.e. fixing a target for the real blood flow $q_{bREAL}=q_{bT}$.

5.3) as 1.3).

5.4) as 1.4).

| CASE 6 | | |
|---|---|---|
| Condition | Hct(0) (initial hematocrit) | Type of needle/vascular access |
| CASE 6 | KNOWN | UNKNOWN |

Let us suppose we do not know the type of needle (or vascular access), and that we cannot identify it through any previously known type. This is a "special case" relating to CASE 5, where we know the initial hematocrit and it is therefore not necessary to estimate its value.

We can proceed as follows:

6.1) as 1.1).

6.2) Identification of the type of needle (or vascular access).

The velocity of the blood pump is varied, the values of arterial pressure measured and the values of real blood flow calculated from equation (00). We can rewrite equation 1) in the following form, for a generic blood pump velocity value $\omega_i$:

$$P_{am}(0)-P_{ami}=R_{ami} \cdot q_{bREALi}=R_{Poiseuille} \cdot (\tilde{\alpha}_1 \cdot Hct(0) \cdot q_{bREALi}+\tilde{\alpha}_0) \cdot q_{bREALi}$$

At this point, by applying any one of the parameter identification methods, the two unknown parameters can be found (angular coefficient and original ordinate $R_{Poiseuille} \cdot \tilde{\alpha}_1$ e $R_{Poiseuille} \cdot \tilde{\alpha}_0$) which describe the vascular access on variation of the blood flow and the hematocrit.

Now we can proceed as in 1.2) of CASE 1, fixing an objective for the real blood flow $q_{bREAL}=q_{bT}$.

6.3) as 1.3).

6.4) as 1.4).

The invention offers important advantages.

By exploiting the knowledge of the system S constituted by the peristaltic pump, the extracorporeal circuit, the access organ and the patient, we can:

1. directly set the angular velocity ω of the peristaltic pump in order to obtain the desired blood flow $q_{bREAL}$=Qset (analytically resolving the equation system which describes the system S).
2. determine the maximum effective flow compatible with a prefixed arterial pressure threshold value. Knowing this value at the moment of keying in the flow range enables:
   a. a more accurate evaluation of the duration of the dialysis treatment (to ensure that a certain volume of blood is treated);
   b. a reduction in the frequency of arterial pressure alarms when the blood pump velocity is adjusted;
3. automatically modify the velocity on fluctuations in some of the patient parameters and/or advise the operator should the range limits on the flow be incompatible with the limit fixed for arterial pressure ($P_{threshold}$).
4. Estimate the arterial pressure variations corresponding to the changes in peristaltic pump angular velocity and thus set up a more accurate control (in both open and closed-chain operation).
5. Integrate the information coming from the biosensors of the machine (measure of the haemoglobin and plasmatic conductivity) to optimise dialysis prescription.

The invention claimed is:

1. A blood treatment machine comprising:
   an extracorporeal circuit having at least a blood treatment unit, at least an access branch extending between a blood removal zone of a patient and the treatment unit, at least a return branch extending between the treatment unit and a blood return zone to the patient, at least a vascular access organ interpositioned between said branches and a patient's vascular system, and at least a pump associated to the extracorporeal circuit, and
   an apparatus for controlling blood flow in the extracorporeal circuit, the apparatus comprising:
   at least a user interface for enabling a setting of a desired value of blood flow ($q_{bREAL}$) through the access branch and in order to allow entry of at least a datum relating to the vascular access;
   a memory storing a plurality of mathematical relations, each of said mathematical relations having a respective mathematical expression which is a function of the vascular access organ to be used and mathematically linking the blood flow through the access branch with an angular velocity of the pump;
   a control unit, connected to the user interface and the pump, which control unit is programmed for performing a process as follows:

identifying the vascular access;
selecting, from among the plurality of mathematical relations present in the memory, the mathematical relation which corresponds to the identified vascular access;
calculating, using the mathematical relation loaded from said memory, at least one from following values:
a value at which the angular velocity of the pump can be set as a function of a set value for a desired flow ($q_{bREAL}$), and
a theoretical value of the arterial pressure in the arterial branch upstream of the pump, as a mathematical function of the set value for the desired flow ($q_{bREAL}$).

2. The machine of claim 1, wherein each of the plurality of mathematical relations comprises:
a respective first mathematical relation which enables a mathematical calculation of a theoretical arterial pressure value in the arterial branch upstream of the pump, as a mathematical function of the set value for the desired flow ($q_{bREAL}$), and
a respective second mathematical relation which enables a mathematical calculation of a value at which the angular velocity of the pump can be set as a function of the theoretical value of the arterial pressure in the arterial branch upstream of the pump.

3. The machine of claim 2, wherein the first mathematical relation enables a mathematical calculation of a theoretical value of arterial pressure in the arterial branch upstream of the pump as a mathematical function of the set value for the desired flow ($q_{bREAL}$) and the value of at least a parameter relating to the chemical/physical characteristics of the patient's blood.

4. The machine of claim 3, wherein the parameter relating to the chemical/physical characteristics of the patient's blood is a parameter relating to the viscosity of the patient's blood.

5. The machine of claim 4, wherein the parameter relating to the patient's blood viscosity comprises the hematocrit of the patient's blood.

6. The machine of claim 5, wherein said apparatus comprises means for determining the hematocrit in the patient's blood, which means operates on the extracorporeal circuit and is connected to the control unit.

7. The machine of claim 6, wherein the means for determining the hematocrit of the patient's blood comprises means for measuring a hematic concentration of hemoglobin and a plasma concentration of sodium, the control unit estimating a value of hematocrit based on the hematic concentration of hemoglobin and the plasma concentration of sodium.

8. The machine of claim 6, wherein the control unit is programmed for verifying, at regular time intervals during the extracorporeal treatment, a value of the parameter relating to the chemical/physical characteristics of the patient's blood, and mathematically recalculating corresponding theoretical values of the arterial pressure in the arterial branch upstream of the pump as a mathematical function of the set value for the desired flow ($q_{bREAL}$) and the value of the parameter at successive moments.

9. The machine of claim 1, wherein the user interface enables entry of an identifying datum of the vascular access to be used, the control unit associating to said vascular access identifying datum the respective mathematical relation from among the plurality of mathematical relations.

10. The machine of claim 1, wherein the user interface enables entry of a datum indicating that the identity of the vascular access is not known, the control unit being programmed to activate an automatic identification procedure of the vascular access, comprising following stages:
varying the angular velocity of the pump;
determining a plurality of real pressure values upstream of the pump, each being relative to an angular velocity of the pump;
identifying, using the real pressure values, a mathematical relation from the plurality of mathematical relations which corresponds to the used vascular access.

11. The machine of claim 1, wherein the control unit is programmed to calculate, using the mathematical relation loaded from the memory, a value at which to set the angular velocity of the pump as a function of the set value for the desired flow ($q_{bREAL}$), and to set the angular velocity of the pump at the calculated value.

12. The machine of claim 1, wherein the control unit is programmed to calculate, using the mathematical relation loaded from the memory, a theoretical value of the arterial pressure in the arterial branch upstream of the pump, as a mathematical function of the set value for the desired flow ($q_{bREAL}$), and to compare the calculated value with an acceptable interval.

13. The machine of claim 12, wherein following the comparison the control unit is programmed to signal whether the theoretical value of the arterial pressure is below a prefixed threshold and to calculate, using the mathematical relation, the angular velocity of the pump and the real flow corresponding to an arterial pressure equal to the prefixed threshold.

14. The machine of claim 12, wherein if after the comparison the control unit has revealed that the theoretical value of the arterial pressure is greater than a prefixed threshold, the control unit is programmed to calculate the limit angular velocity of the pump and the limit real flow corresponding to a pressure which is equal to the prefixed threshold.

15. The machine of claim 14, wherein the control unit is programmed to transmit to the user interface and to visualise on the user interface the value of the limit real flow, which it is possible to reach without falling below the prefixed threshold of arterial pressure.

* * * * *